United States Patent [19]

Koenig et al.

[11] Patent Number: 5,191,098
[45] Date of Patent: Mar. 2, 1993

[54] CONTINUOUS PROCESS FOR PREPARATION OF AQUEOUS DISPERSIONS OF METAL SOAPS

[75] Inventors: H. Steve Koenig, North Wales, Pa.; Gary L. Speenburgh, Parsippany, N.J.

[73] Assignee: Henkel Corporation, Ambler, Pa.

[21] Appl. No.: 803,771

[22] Filed: Dec. 5, 1991

Related U.S. Application Data

[63] Continuation of Ser. No. 385,754, Jul. 26, 1989, abandoned.

[51] Int. Cl.⁵ .............................................. C07C 51/00
[52] U.S. Cl. .................................................... 554/156
[58] Field of Search ....................... 260/414; 554/156

[56] References Cited

U.S. PATENT DOCUMENTS

| | | | |
|---|---|---|---|
| 3,803,188 | 4/1974 | Scott et al. | 260/413 |
| 4,060,535 | 11/1977 | Cinco | 260/414 |
| 4,307,027 | 12/1981 | Borzelli et al. | 260/413 |

FOREIGN PATENT DOCUMENTS

| | | |
|---|---|---|
| 0251900 | 1/1987 | German Democratic Rep. .................... 260/414 |
| A1053805 | 1/1967 | United Kingdom . |
| A1074093 | 6/1967 | United Kingdom . |

OTHER PUBLICATIONS

Chemical Abstracts, vol. 107, #17, 1987, 153927k; abstract of DD 241,900.
Patent Abstracts of Japan vol. 11 No. 232 Kohon 62-4551 Jul. 29, 1987.

Primary Examiner—José G. Dees
Assistant Examiner—Deborah D. Carr
Attorney, Agent, or Firm—Ernest G. Szoke; Wayne C. Jaeschke; Daniel S. Ortiz

[57] ABSTRACT

The invention is a process for preparing an aqueous dispersion of a metal soap by reacting a metal oxide or hydroxide with an organic acid in the presence of a dispersing agent in a media mill.

16 Claims, 2 Drawing Sheets

CONTINUOUS PROCESS FOR PREPARATION OF AQUEOUS DISPERSIONS OF METAL SOAPS

This application is a continuation of application Ser. No. 07/385,754 filed on Jul. 26, 1989, now abandoned.

FIELD OF THE INVENTION

The invention is a continuous process for the production of aqueous dispersions of insoluble metal salts of organic acids and particularly (herein after noted as metal soaps) insoluble metal salts of higher fatty acids. The dispersions of the metal soaps can be utilized as prepared or they can be dried to produce finely divided particulate metal soaps.

Background of the Invention

Metal soaps have found many uses in industry. They generally possess many of the desirable properties of the acids from which the metal soaps are manufactured. Some applications of the metal soaps require that they be prepared in a form of a stable aqueous dispersion. The aqueous dispersions generally comprise the metal soap, water and dispersing agents for the metal soap. The dispersing agent is generally a surfactant or mixture of surfactants which are generally of the anionic and the nonionic type.

DESCRIPTION OF RELATED ART

Metal soap dispersions are available commercially at solid contents of from about 35 to about 75 percent by weight. The aqueous dispersions typically contain about 30 to about 60 percent metal soap, the remaining solids comprising emulsifiers, dispersion aids and other processing aids. The additives are included to enhance the production process for the metal soap or the end-use of the product.

Aqueous dispersions of metal soaps have been prepared in the past by three methods.

One of the oldest methods comprises reacting the organic acid with an oxide or hydroxide of the metal, in the presence of a small amount of water, to form a solid metal soap of the acid, grinding the metal soap and dispersing the ground material in water by means of a dispersing agent.

More recent processes prepare the dispersion of the metal soap by reacting a fatty acid with an oxide or hydroxide of the metal in the presence of a dispersing agent and the water in which the metal soap of the fatty acid is to be dispersed. The processes are generally batch processes and require several hours to complete the reaction. The dispersions prepared by the known methods generally require that the dispersion be milled to provide a stable dispersion having particles within a required particle size range.

The metal soaps have been prepared by a double decomposition method wherein the metal soap is precipitated from an aqueous solution by reaction of an alkali metal salt of the fatty acid with an acid salt of the metal used to form the metal soap. The metal soap precipitates as a fluffy material, can be recovered from the aqueous medium washed free of the alkali metal salts then dispersed in an aqueous medium to form a dispersion. The known processes are generally batch processes and require milling of the dispersion to provide a stable product having dispersed therein metal soap of a small particle size.

There are many patents which disclose processes for preparing metal soaps and dispersions of metal soaps.

Patents such as U.S. Pat. No(s). 2,660,568, 3,803,188, 4,060,535, 4,307,027, Japanese Kokai No. 51/34904 (Mar. 25, 1976), Kokai No. 54/8606 (Jan. 23, 1979), Kokai No. 59/51236 (Mar. 24, 1984) disclose processes for preparing metal soaps and aqueous dispersions of metal soaps. In particular U.S. Pat. No. 3,803,188 discloses the three general methods used to prepare metal soaps.

A batch process is disclosed in East German Pat. No. 106629, Patented Jun. 20, 1974. The patent discloses a process for making dispersions of metal soaps such as calcium, zinc or lead stearate. The process comprises preparing a mixture of water, a dispersing agent and the hydroxide of the metal with acetic acid at a temperature above the melting point of the fatty acid in a Cowles Disolver and introducing the fatty acid into the mixture at a temperature above its melting point.

A continuous process for preparing dispersions of metal soaps is disclosed in East German Pat. No. 241900. The process discloses continuously introducing a suspension of the metal oxide or metal hydroxide into a cascade of stirred reactors. The fatty acid is introduced into each of the stirred reactors depending upon the concentration of the fatty acid at that point of the process. The process is relatively complex in that the concentration of the fatty acid in a plurality of reactors must be monitored and the addition of the fatty acid into each of the series of reactors must be controlled. The process provides a relatively long residence time of the dispersion in the system.

BRIEF DESCRIPTION OF THE INVENTION

The invention is a continuous single step process for the production of aqueous, metal soap dispersions which comprises continuously introducing an aqueous suspension of an oxide or hydroxide of the metal, at least one dispersing agent and a molten organic acid into a media mill and removing a dispersion of the metal soap from the media mill. The process of the present invention is carried out at a residence time in the range of 1 to 55 minutes and produces a dispersion having a low-free fatty acid content. The process does not require additional milling to provide an aqueous dispersion. The dispersion is stable has a small particle size and substantially no oversized material.

DETAILED DESCRIPTION OF THE INVENTION

Figure 1:
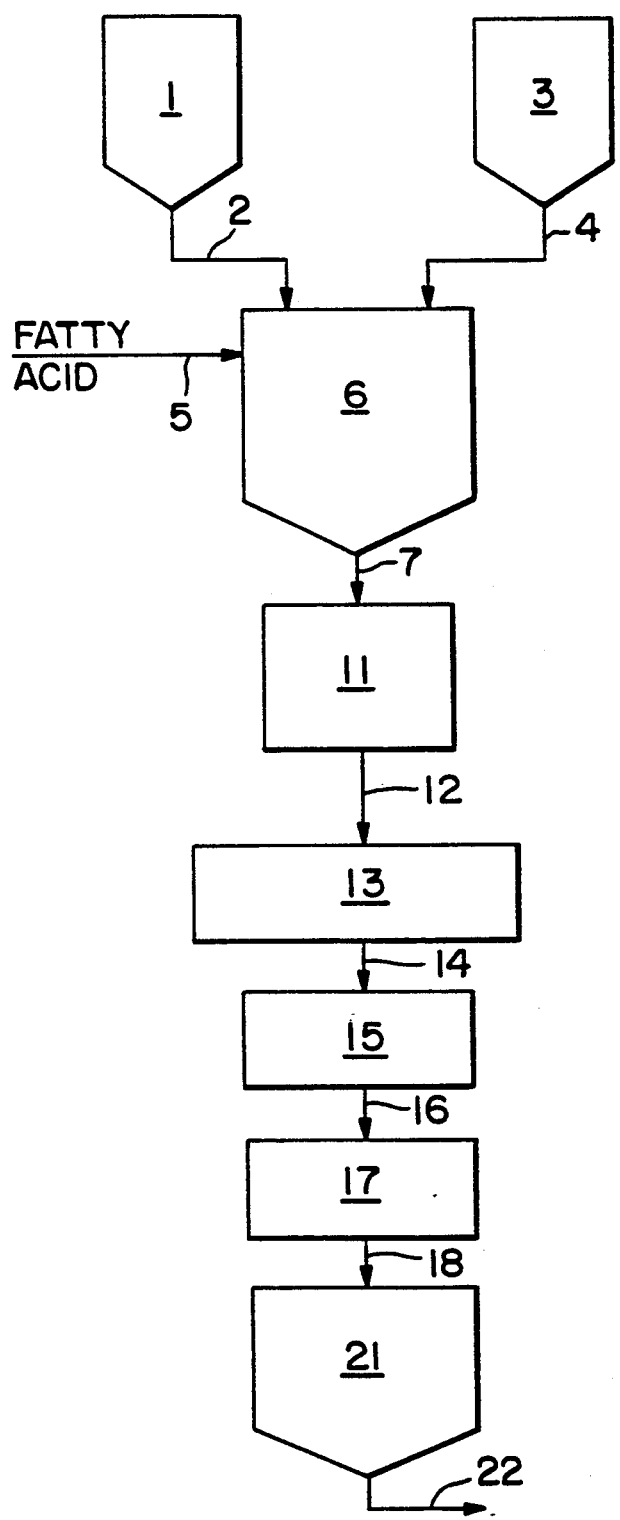
FIG. 1 is a schematic representation of a typical prior art process for preparing aqueous dispersions of metal soaps.

The advantages of the process of the present invention can be better understood by comparison with a batch process which is known in the prior art. FIG. 1 is a schematic representation of a prior art batch process for preparing a calcium fatty acid soap dispersion. A dispersing agent or mixture of dispersing agents is prepared in tank 1 and introduced into the reactor 6 through line 2. A suspension of lime in water is prepared in tank 3 and introduced into reactor 6 through line 4. Reactor 6 is a well agitated reactor. After the dispersing agent and the lime suspension had been introduced into reactor 6, the aqueous mixture is heated to a temperature near the melting point of the fatty acid. Molten fatty acid is then introduced through line 5 into the agitated suspension of the calcium hydroxide and the agitation continued until the fatty acid is substantially reacted to the desired metal soap. The reaction generally requires about 1 to about 10 hours to complete. The temperature in the reactor is controlled by cooling means in the reactor jacket.

After the reaction is completed, the dispersion is passed from the reactor 6 through line 7 to holding tank 11. Holding tank 11 is necessary to permit the reactor to again be filled with reactants and another batch of the dispersion of the metal soap prepared. The dispersion from holding tank 11 is then introduced through line 12 into a milling or grinding means 13. The grinding means 13 can comprise one or more grinding means which reduces the particle size of the metal soap dispersion to the required particle size range. Suitable grinding means are known in the art. The ground dispersion then passes through line 14 through heat exchanger 15, and line 16 to size separating means 17. In size separating means 17 the oversize particles in the dispersion are separated from the dispersion and can be returned to the grinding means. The dispersion of the required particle size passing through size separating means 17 passes through line 18 to production holding tank 21. The dispersion is mixed in holding tank 21, sampled and if it meets specifications can be transferred to a storage tank (not shown) through line 22 or transferred for use.

As can be seen from the schematic diagram of a conventional process, the process is a batch one which requires reacting and milling steps and requires a substantial amount of process equipment to accomplish the process.

Figure 2:
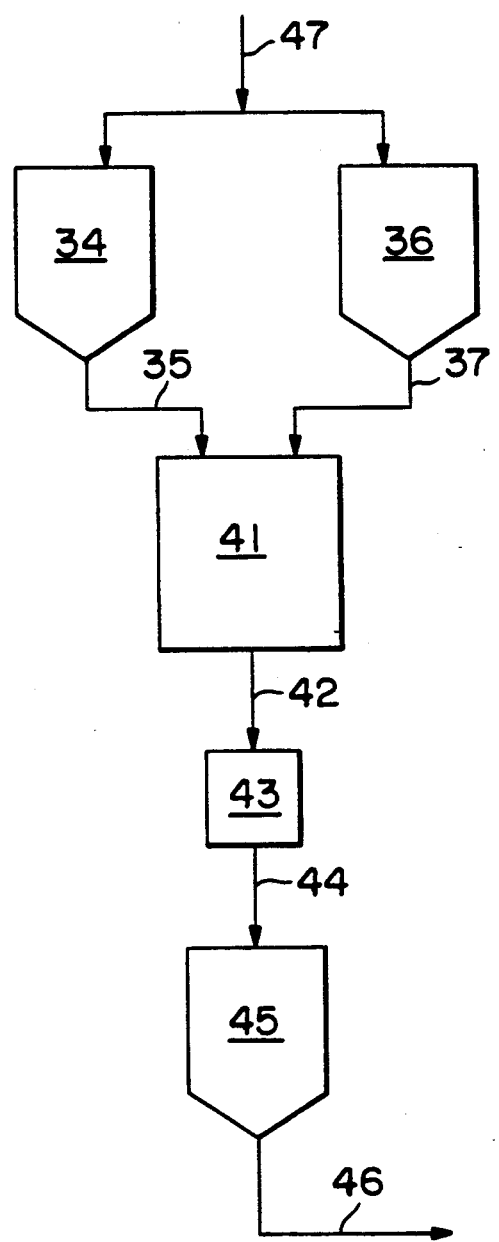
FIG. 2 is a schematic representation of the process of the present invention.

In contrast to the conventional processes for preparing metal soap dispersions, FIG. 2 is a schematic representation of the process of the present invention.

As shown in FIG. 2, a dispersing agent or a mixture of dispersing agents is introduced into the fatty acid in feed tank 34 and into the metal oxide or hydroxide aqueous suspension in tank 36 through line 47 and mixed therewith. The fatty acid, in fatty acid holding tank 34, is in a molten condition. The molten fatty acid is continuously introduced into the reactor 41 through line 35 and the aqueous suspension of the metal oxide or hydroxide in holding tank 36 is continuously introduced through line 37 into reactor 41.

Reactor 41 is a media mill. The temperature in the media mill can be controlled by circulating cooling fluid in the jacket or internally arranged cooling means. In the mill, a media is caused to move about and contact the particles of the fatty acid and the metal oxide or hydroxide to cause them to react and to provide dispersed particles in a suitable particle size range.

The residence time in the media mill is relatively short and ranges from about 1 to less than about 55 minutes. Preferably from about 2 to about 20 minutes. The dispersion then passes from the media mill 41 through line 42 through heat exchanger 43 and line 44 to holding tank 45. In holding tank 45, the dispersion is sampled to determine if it meets the proper particle size, viscosity, free acid and other specifications and is then passed to a storage tank (not shown) through line 46.

The particle size at the outlet of the media mill reactor is uniform and generally no screening or sizing operation is required. However, as a safety measure, should something malfunction in the system, a sizing means can be introduced into line 44 between heat exchanger 43 and holding tank 45.

As can be seen from a comparison of the schematic of the process of the present invention and the schematic for the batch process, the process of the present invention is simpler, requires less equipment and can be operated at a lower cost than the known processes.

Soaps of metals such as aluminum, barium, calcium, cadmium, cobalt, copper, iron, lead, lithium, magnesium, manganese, nickel, strontium and zinc can be prepared by the process of the present invention. Generally, the process of the present invention can be adapted to provide dispersions of the metal soaps which can be prepared by the batch processes of the prior art.

The fatty acids which can be utilized to prepare metal soap dispersions, by the process of the present invention generally contain from about 8 to about 30 and preferably about 10 to about 24 carbon atoms. The acids can be saturated or unsaturated, straight chain or branched chain. Dispersions of metal soaps of fatty acids such as octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, hencosanoic acid, docosanoic acid, and their isomers can be prepared by the process of the invention. Dispersions of soaps of the unsaturated fatty acids such as the octenoic acids, nonenoic acids, decenoic acids, undecenoic acids, dodecenoic acids, tridecenoic acids, tetradecenoic acids, pentadecenoic acids, hexadecenoic acids, heptadecenoic acids, octadecenoic acides, nonadecenoic acids, eicosenoic acids, docosenoic acids, tetracosenoic acids, and their isomers can be prepared by the process of the evention. Dispersions of metal soaps of dienoic, trienoic and, tetraenoic acids having from about 8 to about 24 carbon atoms can be prepared by the process of the invention.

Dispersions of metal soaps of hydroxy substituted fatty acids having from about 8 to about 30 carbon atoms can be prepared by the process of the invention. Dispersions of water insoluble soaps of alicyclic and aromatic acids can also be prepared by the process of the invention.

Useful surfactants or dispersing agents include anoinic surfactants such as ethoxylated alkyl phenol sulfates and sulfonates, fatty acid sulfates and sulfonates, petroleum sulfates and sulfonates, alcohol sulfates, ethoxylated alcohol sulfates, fatty acid ester sulfates, alkyl benzene sulfonates, alkyl napthalene sulfonates, sulfosuccinates, taurates, betaines, carboxylated alcohol ethoxylates and the like. Nonionic surfactants such as ethoxylated alcohols, ethoxylated alkyl phenols, ethoxylated amines or amides, ethoxylated fatty acid esters, propylene oxide-ethylene oxide, random and block copolymers, fatty esters, polyethylene glycol ethers and the like can be used as dispersing agents in the practice of the invention.

The dispersing agents are present in a sufficient amount to provide a stable dispersion. Generally, the dispersing agent or mixture of dispersing agents is in the range of from about 0.5 to about 20% by weight of the dispersion and preferably in the range of about 1.5 to about 10% by weight of the dispersion. The amount and type of dispersing agent is not critical except that it must be capable of providing a stable dispersions. Special user requirements may require the use of special dispersing agents.

The process can also be utilized to prepare dispersions of metal soaps from aromatic and alicyclic acids. The process can be utilized to prepare metal soaps of aromatic acids such as naphthenic acid and the like. Process of the present invention can be generally utilized to prepare dispersions of metal salts of acids which provide water insoluble metal salts (metal soaps).

The dispersing agents used in the process of the present invention are conventional and well known in the art. Both anionic and nonionic surfactants can be used to prepare aqueous dispersions of metal soaps. Mixtures of anionic and nonionic surfactants are preferred since the advantageous properties of each of the surfactants is retained in the mixture. However, some applications require special dispersing agents to meet special end use requirements.

In the process of the present invention, the dispersing agents can be added to the aqueous suspension of the metal hydroxide or oxide, can be added to the molten fatty acid, can be added to each of the reactants or can be added directly into the reactor along with the suspension of the metal oxide or hydroxide in water and the fatty acid. However, it is preferred that the dispersing agents be introduced in admixture with at least one of the suspension of the metal oxide or hydroxide in water or with the molten fatty acid. The premixing of the dispersing agent with the reactants permits the introduction of the dispersing agent into the reactor in a metered amount without the requirement that an additional stream of reactants be metered into the reactor. For special requirements, additional dispersing agents or surfactants can be introduced into the dispersion leaving the media mill reaction zone. However, at least part of the dispersing agent should be introduced into the media mill reactor alone or preferably mixed with at least one of the fatty acid or the metal hydroxide or oxide dispersion.

The process of the present invention generally uses about a stoichiometric amount of multivalent metal compound to neutralize the fatty acid. A small excess or deficiency of metal hydroxide or oxide can be used to meet user requirements. Generally a small excess of about 1 to about 10% on an equivalent basis of the metal hydroxide or oxide is used. The dispersion generally contain from about 25% to about 65% by weight water preferably from about 30 to about 55% by weight water based on the weight of the dispersion.

The process can be operated over a broad temperature range. A temperature of from about 25°–100° C. can be used. However a temperature in the range of about 35° C. to about 95° C. is preferred and most preferred is temperatures in the range of about 50° C. to about 95° C. Temperatures above 100° C. can be used but require special pressure equipment and product handling. Temperatures in the range of about 50° C. to about 95° C. provide for a rapid reaction and produce a dispersion with low fatty acid content. Higher temperatures are not required. The reaction temperature does not have to be above the melting point of the acid or soap.

The media mill utilized as the reaction zone in the process of the present invention comprises a vessel containing particulate material which tumble or move in the vessel. The particulate material can be moved in the vessel interior by rotating or vibrating the vessel or by providing means which stir the media. When the media or particulate material is moved by vibrating or stirring, the vessel can be arranged horizontally or vertically. Due to the flexibility in arranging the feed introduction and product discharge means, a horizontally arranged media mill reaction zone is preferred.

Media mill as used herein refers to grinding and milling devices which utilize the movement of solid particles known as media within the apparatus to impart energy to the material being milled. Movement of the media can be achieved by rotating or vibrating the vessel containing the media. Movement of the media can also be provided by stirring means provided in the vessel or reaction zone. A combination of stirring and vessel movement can also be used.

In a preferred embodiment, a horizontally arranged media mill manufactured by Premier Mill Corporation, charged with glass or ceramic beads is used as the reaction zone for the process of the invention.

The mill is charged with media, with a particle size in the range of from about 1 to about 3 mm in diameter. The media can be glass, ceramic or metal particles or the like. The process of the present invention has been found to achieve excellent results utilizing media comprising glass beads of about 1.5–2.5 mm in diameter.

The void volume in the mill is generally filled from about 50 to about 95 percent with the grinding media. Preferably the mill is charged with from about 62 to 90 percent of the void volume with the grinding media.

A preferred apparatus, the Premier Mill comprises a horizontally arranged vessel with a rotating means for stirring the media. The rotating means generally rotates at from about 1000 to about 3000 revolutions per minute. Lower or higher rotation speeds may be utilized and is dependent upon the media being used, and the size of the apparatus. The rotating device contacts the media and causes the media to move within the reaction zone. The impact of the media with the particles of the fatty acid and the metal oxide or hydroxide and the precipitated metals soap causes the reaction to proceed at a rapid rate and to produce a dispersion with a small particle size.

The following examples are presented to illustrate the process of the invention. The examples are for illustration only and are not intended to be a limitation to the invention. The process is illustrated by an embodiment for production of calcium stearate but other metal soaps can be prepared by the process.

In the examples, a suspension of calcium hydroxide in the water for the dispersion was prepared. A portion of the dispersing agents was added to the suspension. The suspension of calcium hydroxide was maintained at 20 to 30 degrees centigrade.

A portion of the dispersing agent was mixed with molten stearic acid at a temperature of 80 to 85 degrees centigrade.

The reaction zone was a horizontally arranged Premier Super Mill ™ with a free volume of 15 liters charged with 1.5 or 2 millimeter diameter glass beads or 1.7 or 2 mm diameter zirconium silicate beads or 1.7 mm zirconium oxide beads. The mill comprised a shell with a removable end closure which carried a rotating milling shaft. The milling shaft carried discs which when rotated imparted energy and movement to the beads. The rate of rotation of the milling shaft was varied from 1100 to 1650 r.p.m.

The mill was heated to 50° to 55° C. by passing hot water through the mill. When the mill temperature reached 50° to 55° centrigade, the flow of hot water was stopped, the milling shaft was started rotating and the flow of calcium hydroxide suspension and molten fatty acid was started into the mill. The temperature of the dispersion leaving the mill was controlled by flow of cooling water through the mill shell.

The examples show the composition of the feed streams, the feed rate, retention time, and product temperature. The table presents a summary of the data and the properties of the dispersions. The examples were carried out according to the process illustrated in FIG. 2.

EXAMPLE 1

Lime Slurry Feed

702 Lbs Water
92 Lbs Hydrated Lime (MV300/Mississippi Lime Co.)
2.5 Lbs Ethoxylated Nonyl Phenol (Hyonic ® PE-100/Henkel Corp.)
4.0 Lbs sodium salt of an Alkyl Aryl Sulfonate (Witconate ® 1238/Witco)

Agitation was started and the temperature adjusted to 20°-30° C.

Fatty Acid Feed

650 Lbs $C_{18}$ fatty acid (Industrene ® 7018/Witco Chemical)
37 Lbs Ethoxylated Nonyl Phenol (Hyonic ® PE-100/Henkel Corp.)
3.5 Lbs $C_{36}$-$C_{54}$ dimer/trimer fatty acid (Empol ® 1022/Emery Chemicals)

The vessel was heated until the charge was molten. Agitation was started and the temperature adjusted to 80°-85° C.

The Premier Mill was charged with 2 mm glass beads to 90% of the available volume. The mill was preheated to 55° C. bypassing hot water through the mill chamber. Simultaneously, the mill shaft was started at 1650 RPM, lime slurry feed was started at 0.96 lb/min., and molten fatty acid feed was started at 0.76 lb/min. rate. The average retention time (ART) in the mill was 8.9 min. The temperature of the exiting material was controlled at 70° C. by cooling water applied to the jacket of the mill. The product was cooled to room temperature.

EXAMPLE 2

Lime Slurry Feed

750 Lbs Water
92 Lbs Hydrated Lime (MV300/Mississippi Lime Co.)
2.5 Lbs Ethoxylated Nonyl Phenol (Hyonic ® PE-100/Henkel Corp.)
4.0 Lbs sodium salt of an Alkyl Aryl Sulfonate (Witconate ® 1238/Witco)
48 Lbs Peg 600 Monolaurate (Nopalcol ®6-L/Henkel Corp.)

Agitation was started and the temperature adjusted to 20°-30° C.

Fatty Acid Feed

650 Lbs $C_{18}$ fatty acid (Industrene ® 7018/Witco Chemical)
37 Lbs Ethoxylated Nonyl Phenol (Hyonic ® PE-100/Henkel Corp.)
3.5 Lbs $C_{36}$-$C_{54}$ dimer/trimer fatty acid (Empol ® 1022/Emery Chemicals) The vessel was heated until the charge was molten. Agitation was started and the temperature adjusted to 80°-85° C.

The Premier Mill was charged with 2 mm glass beads to 60% of the available volume. The mill was preheated to 55° C. by passing hot water through the mill chamber. Simultaneously, the mill shaft was started at 1100 RPM, lime slurry feed was started at 1.01 lb/min., and molten fatty acid feed was started at 0.76 lb/min. rate. The average retention time (ART) in the mill was 12.4 min. The temperature of the exiting material was controlled at 85° C. by cooling water applied to the jacket of the mill. The product was cooled to room temperature by passing through a heat exchanger.

EXAMPLE 3

Lime Slurry Feed

750 Lbs Water
92 Lbs Hydrated Lime (MV300/Mississippi Lime Co.)
2.5 Lbs Ethoxylated Nonyl Phenol (Hyonic ® PE-100/Henkel Corp.)
4.0 Lbs sodium salt of an Alkyl Aryl Sulfonate (Witconate ® 1238/Witco)
48 Lbs Peg 600 Monolaurate (Nopalcol ® 6-L/Henkel Corp.

Agitation was started and the temperature adjusted to 20°-30° C.

Fatty Acid Feed

650 Lbs $C_{18}$ fatty acid (Industrene ® 7018/Witco Chemical)
37 Lbs Ethoxylated Nonyl Phenol (Hyonic ® PE-100/Henkel Corp.)
3.5 Lbs $C_{36}$-$C_{54}$ dimer/trimer fatty acid (Empol ® 1022/Emery Chemicals)

The vessel was heated until the charge was molten. Agitation was started and the temperature adjusted to 80°-85° C.

The Premier Mill was charged with 2 mm glass beads to 60% of the available volume. The mill was preheated to 55° C. by passing hot water through the mill chamber. Simultaneously, the mill shaft was started at 1650 RPM, lime slurry feed was started at 2.00 lb/min., and molten fatty acid feed was started at 1.53 lb/min. rate. The average retention time (ART) in the mill was 5.2 min. The temperature of the exiting material was controlled at 85° C. by cooling water applied to the jacket of the mill. The product was cooled to room temperature by passing through a heat exchanger.

EXAMPLE 4

Lime Slurry Feed

750 Lbs Water
92 Lbs Hydrated

Lime (MV300/Mississippi Lime Co.)
2.5 Lbs Ethoxylated Nonyl Phenol (Hyonic ® PE-100/Henkel Corp.)
4.0 Lbs sodium salt of an Alkyl Aryl Sulfonate (Witconate ® 1238/Witco)
48 Lbs Peg 600 Monolaurate (Nopalcol ® 6-L/Henkel Corp.

Agitation was started and the temperature adjusted to 20°-30° C.

Fatty Acid Feed

650 Lbs $C_{18}$ fatty acid (Industrene ® 7018/Witco Chemical)
37 Lbs Ethoxylated Nonyl Phenol (Hyonic ® PE-100/Henkel Corp.)
3.5 Lbs $C_{36}$-$C_{54}$ dimer/trimer fatty acid (Empol ® 1022/Emery Chemicals)

The vessel was heated until the charge was molten. Agitation was started and the temperature adjusted to 80°-85° C.

The Premier Mill was charged with 2 mm glass beads to 60% of the available volume. The mill was preheated to 55° C. by passing hot water through the mill chamber. Simultaneously, the mill shaft was started at 1100 RPM, lime slurry feed was started at 2.10 lb/min., and molten fatty acid feed was started at 1.53 lb/min. rate. The average retention time (ART) in the mill was 6.1 min. The temperature of the exiting material was controlled at 55° C. by cooling water applied to the jacket of the mill. The product was cooled to room temperature by passing through a heat exchanger.

EXAMPLE 5

Lime Slurry Feed

750 Lbs Water
92 Lbs Hydrated

Lime (MV300/Mississippi Lime Co.)

2.5 Lbs Ethoxylated Nonyl Phenol (Hyonic® PE-100/Henkel Corp.)
4.0 Lbs sodium salt of an Alkyl Aryl Sulfonate (Witconate® 1238/Witco)
48 Lbs Peg 600 Monolaurate (Nopalcol® 6-L/Henkel Corp.)

Agitation was started and the temperature adjusted to 20°-30° C.

Fatty Acid Feed

650 Lbs $C_{18}$ fatty acid (Industrene® 7018/Witco Chemical)
37 Lbs Ethoxylated Nonyl Phenol (Hyonic® PE-100/Henkel Corp.)
3.5 Lbs $C_{36}$-$C_{54}$ dimer/trimer fatty acid (Empol® 1022/Emery Chemicals)

The vessel was heated until the charge was molten. Agitation was started and the temperature adjusted to 80°-85° C.

The Premier Mill was charged with 2 mm glass beads to 60% of the available volume. The mill was preheated to 55° C. by passing hot water through the mill chamber. Simultaneously, the mill shaft was started at 1100 RPM, lime slurry feed was started at 3.58 lb/min., and molten fatty acid feed was started at 2.32 lb/min. rate. The average retention time (ART) in the mill was 3.6 min. The temperature of the exiting material was controlled at 80° C. by cooling water applied to the jacket of the mill. The product was cooled to room temperature by passing through a heat exchanger.

EXAMPLE 6

Lime Slurry Feed

750 Lbs Water
92 Lbs Hydrated Lime (MV300/Mississippi Lime Co.)
39.5 Lbs Ethoxylated Nonyl Phenol (Hyonic® PE-100/Henkel Corp.)
4.0 Lbs sodium salt of an Alkyl Aryl Sulfonate (Witconate® 1238/Witco)
48 Lbs Peg 600 Monolaurate (Nopalcol® 6-l/Henkel Corp.)

Agitation was started and the temperature adjusted to 20°-30° C.

Fatty Acid Feed

650 Lbs $C_{18}$ fatty acid (Industrene® 7018/Witco Chemical)
3.5 Lbs $C_{36}$-$C_{54}$ dimer/trimer fatty acid (Empol® 1022/Emery Chemicals)

The vessel was heated until charge was molten. Agitation was started and the temperature adjusted to 80°-85° C.

The Premier Mill was charged with 2 mm glass beads to 60% of the available volume. The mill was preheated to 55° C. by passing hot water through the mill chamber. Simultaneously, the mill shaft was started at 1650 RPM, lime slurry feed was started at 3.03 lb/min., and molten fatty acid feed was started at 2.16 lb/min. rate. The average retention time (ART) in the mill was 4.0 min. The temperature of the exiting material was controlled at 60° C. by cooling water applied to the jacket of the mill. The product was cooled to room temperature by passing through a heat exchanger.

EXAMPLE 7

Lime Slurry Feed

725 Lbs Water
92 Lbs Hydrated

Lime (MV300/Mississippi Lime Co.)

39.5 Lbs Ethoxylated Nonyl Phenol (Hyonic® PE-100/Henkel Corp.)
4.0 Lbs sodium salt of an Alkyl Aryl Sulfonate (Witconate® 1238/Witco)
22.5 Lbs Peg 600 Monolaurate (Nopalcol®6-L/Henkel Corp.)

Agitation was started and the temperature adjusted to 20°-30° C.

Fatty Acid Feed

650 Lbs $C_{18}$ fatty acid (Industrene® 7018/Witco Chemical)
3.5 Lbs $C_{36}$-$C_{54}$ dimer/trimer fatty acid (Empol® 1022/Emery Chemicals)

The vessel was heated until the charge was molten. Agitation was started and the temperature adjusted to 80°-85° C.

Additive Feed

22 Lbs Water
22 Lbs Peg 600 Monolaurate (Nopalcol 6-L/Henkel Corp.)

The Premier Mill was charged with 2 mm glass beads to 60% of the available volume. The mill was preheated to 55° C. by passing hot water through the mill chamber. Simultaneously, the mill shaft was started at 1650 RPM, lime slurry feed was started at 3.30 lb/min., and molten fatty acid feed was started at 2.16 lb/min. rate. The average retention time (ART) in the mill was 3.8 min. The temperature of the exiting material was controlled at 70° C. by cooling water applied to the jacket of the mill. The product was cool to room temperature by passing through a heat exchanger. The product from the heat exchanger was post blended with the additive feed as follows:

97 Lbs of heat exchanger output
3 Lbs of the additive feed

The blending was done at 20°-30° C.

EXAMPLE 8

Lime Slurry Feed

560 Lbs Water
92 Lbs Hydrated

Lime (MV300/Mississippi Lime Co.)

39.5 Lbs Ethoxylated Nonyl Phenol (Hyonic® PE-100/Henkel Corp.)
4.0 Lbs sodium salt of an Alkyl Aryl Sulfonate (Witconate® 1238/Witco)
22.5 Lbs Peg 600 Monolaurate (Nopalcol®6-L/Henkel Corp.)

Agitation was started and the temperature adjusted to 20°–30° C.

Fatty Acid Feed

650 Lbs $C_{18}$ fatty acid (Industrene® 7018/Witco Chemical)
3.5 Lbs $C_{36}$–$C_{54}$ dimer/trimer fatty acid (Empol® 1022/Emery Chemicals)

The vessel was heated until the charge was molten. Agitation was started and the temperature adjusted to 80°–85° C.

The Premier Mill was charged with 2 mm glass beads to 60% of the available volume. The mill was preheated to 55° C. by passing hot water through the mill chamber. Simultaneously, the mill shaft was started at 1650 RPM, lime slurry feed was started at 2.56 lb/min., and molten fatty acid feed was started at 2.18 lb/min. rate. The average retention time (ART) in the mill was 4.2 min. The temperature of the exiting material was controlled at 70° C. by cooling water applied to the jacket of the mill. The product was cooled to room temperature by passing through a heat exchanger.

EXAMPLE 9

Lime Slurry Feed

404 Lbs Water
69 Lbs Hydrated Lime (MV300/Mississippi Lime Co.)
27.5 Lbs ethoxylated nonyl phenol (Hyonic® PE-100/Henkel Corp.)
1.6 Lbs sodium salt of an Alkyl Aryl Sulfonate (Witconate® 1238/Witco)
5.0 Lbs Peg 600 Monolaurate (Nopalcol®6-L/Henkel Corp.)

Agitation was started and the temperature adjusted to 20°–30° C.

Fatty Acid Feed

444 Lbs $C_{18}$ fatty acid (Industrene® 7018/Witco Chemical)
2.3 Lbs $C_{36}$–$C_{54}$ dimer/trimer fatty acid (Empol® 1022/Emery Chemical)

The vessel was heated until the charge was molten, agitation was started and the temperature adjusted to 80°–85° C.

Additive Feed

16 Lbs Water
30 Lbs Peg 600 Monolaurate (Nopalcol®6-l/Henkel Corp.)
0.5 Lbs Benzisothiazolin-3-One (Proxel® GXL/ICI Americas)

The components were charged and mixed at 20°–30° C.

The Premier Mill was charged with 2 mm glass beads to 65% of the available volume. The mill was preheated to 55° C. by passing hot water through the mill chamber. Simultaneously, the mill shaft was started at 1650 RPM, lime slurry feed was started at 2.70 lb/min., and molten fatty acid feed was started at 2.53 lb/min. rate. The average retention time (ART) in the mill was 3.8 min. The temperature of the exiting material was controlled at 75° C. by cooling water applied to the jacket of the mill. As the material exited the mill it was passed through a static mixer where 0.20 lb/min. of the additive feed was added. The product was then cooled to room temperature by passing through a heat exchanger.

EXAMPLE 10

Lime Slurry Feed

410 Lbs Water
74 Lbs Hydrated

Lime (MV300/Mississippi Lime Co.)

1.6 Lbs sodium salt of an Alkyl Aryl Sulfonate (Witconate® 1238/Witco)
5.2 Lbs Peg 600 Monolaurate (Nopalcol®6-L/Henkel Corp.)

Agitation was started and temperature adjusted to 20°–30° C.

Fatty Acid Feed

436 Lbs $C_{18}$ fatty acid (Industrene® 7018/Witco Chemical)
27.5 Lbs Ethoxylated Nonyl Phenol (Hyonic® PE-100/Henkel Corp.
2.2 Lbs $C_{36}$–$C_{54}$ dimer/trimer fatty acid (Empol® 1022/Emery Chemical)

The vessel was heated until charge was molten, then agitation was started and temp adjusted to 80°–85° C.

Additive Feed

16 Lbs Water
30 Lbs Peg 600 Monolaurate (Nopalcol®6-L/Henkel Corp.)
0.5 Lbs Benzisothiazolin-3-One (Proxel®GXL/ICI Americas)

The components were charged and mixed at 20°–30° C.

The Premier Mill was charged with 2 mm glass beads to 65% of the available volume. The mill was preheated to 55° C. by passing hot water thru the mill chamber. Simultaneously, the mill shaft was started at 1650 RPM, lime slurry feed was started at 2.71 lb/min., and molten fatty acid feed was started at 2.53 lb/min. rate. The average retention time (ART) in the mill was 3.8 min. The temperature of the exiting material was controlled at 75° C. by cooling water applied to the jacket of the mill. As the material exited the mill it was passed thru a static mixer where 0.24 lb/min. of the additive composition was added. The product was then cooled to room temperature by passing thru a heat exchanger.

EXAMPLE 11

Lime Slurry Feed

627 Lbs Water
107.4 Lbs Hydrated

Lime (MV300/Mississippi Lime Co.)

7.5 Lbs Peg 600 Monolaurate (Nopalcol® 6-L/Henkel Corp.)

Agitation was started and the temperature adjusted to 20°-30° C.

Fatty Acid Feed

725 Lbs $C_{18}$ fatty acid (Industren ® 7018/Witco Chemical)
51.0 Lbs Ethoxylated Nonyl Phenol (Hyonic ®PE-100/Henkel Corp.)
3.9 Lbs $C_{36}$-$C_{54}$ dimer/trimer fatty acid (Empol ® 1022/Emery Chemicals)
2.7 Lbs sodium salt of an alkyl aryl sulfonate (Witconate ® 1238/Witco)
15.5 Lbs Peg 600 Monolaurate (Nopalcol ® 6-L/Henkel Corp.)

The vessel was heated until the charge was molten, agitation was started and the temperature adjusted to 80°-85° C.

Additive Feed 56.2 Lbs Water
47.4 Lbs Peg 600 Monolaurate (Nopalcol ® 6-L/Henkel Corp.)
0.7 Lbs Benzisothiazolin-3-one (Proxel ® GXL/ICI Americas)

The components were charged and mixed at 20°-30° C.

The Premier Mill was charged with 2 mm zirconium silicate beads to 90% of the available volume. The mill was preheated to 55° C. by passing hot water through the mill chamber. Simultaneously, the mill shaft was started at 1650 RPM, lime slurry feed was started at 2.16 lb/min., and molten fatty acid feed was started at 2.36 lb/min. rate. The average retention time (ART) in the mill was 3.3 min. The temperature of the exiting material was controlled at 85° C. by cooling water applied to the jacket of the mill. As the material exited the mill it was passed through a static mixer where 0.33 lb/min. of the additive feed was added. The product was cooled to room temperature by passing through a heat exchanger.

EXAMPLE 12

Lime Slurry Feed

627 Lbs Water
104.7 Lbs Hydrated Lime (MV300/Mississippi Lime Co.)
7.5 Lbs Peg 600 Monolaurate (Nopalcol ® 6-L/Henkel Corp.)

Agitation was started and the temperature adjusted to 20°-30° C.

Fatty Acid Feed

725 Lbs $C_{18}$ fatty acid (Industrene ® 7018/Witco Chemical)
51.0 Lbs Ethoxylated Nonyl Phenol( Hyonic ®PE-100/Henkel Corp.)
3.9 Lbs $C_{36}$-$C_{54}$ dimer/trimer fatty acid (Empol ® 1022/Emery Chemicals)
2.7 Lbs sodium salt of an alkyl aryl sulfonate (Witconate ® 1238/Witco)
15.5 Lbs Peg 600 Monolaurate (Nopalcol ® 6-L/Henkel Corp.)

The vessel was heated until the charge was molten, agitation was started and the temperature adjusted to 80°-85° C.

Additive Feed 56.2 Lbs Water
47.4 Lbs Peg 600 Monolaurate (Nopalcol ® 6-L/Henkel Corp.)
0.7 Lbs Benzisothiazolin-3-one (Proxel ® GXL/ICI Americas)

The components were charged and mixed at 20°-30° C.

The Premier Mill was charged with 1.7 mm zirconium oxide beads to 80% of the available volume. The mill was preheated to 55° C. by passing hot water through the mill chamber. Simultaneously, the mill shaft was started at 1650 RPM, lime slurry feed was started at 2.18 lb/min., and molten fatty acid feed was started at 2.33 lb/min. rate. The average retention time (ART) in the mill was 3.8 min. The temperature of the exiting material was controlled at 95° C. by cooling water applied to the jacket of the mill. As the material exited the mill it was passed through a static mixer where 0.33 lb/min. of the additive feed was added. The product was cooled to room temperature by passing through a heat exchanger.

EXAMPLE 13

Lime Slurry Feed

542 Lbs Water
92.7 Lbs Hydrated Lime (MV300/Mississippi Lime Co.)
6.5 Lbs Peg 600 Monolaurate (Nopalcol ® 6-L/Henkel Corp.)

Agitation was started and the temperature adjusted to 20°-30° C.

Fatty Acid Feed 648.5 Lbs $C_{18}$ fatty acid (Industrene ® 7018/Witco Chemical)
45.6 Lbs Ethoxylated Non Phenol (Hyonic ® PE-100/Henkel Corp.)
3.5 Lbs $C_{36}$-$C_{54}$ dimer/trimer fatty acid (Empol ® 1022/Emery Chemicals)
2.5 Lbs sodium salt of an alkyl aryl sulfonate (Witconate ® 1238/Witco)

The vessel was heated until the charge was molten, agitation was started and the temperature adjusted to 80°-85° C.

Additive Feed 64.8 Lbs Water
54.4 Lbs Peg 600 Monolaurate (Nopalcol ® 6-L/Henkel Corp.)
0.8 Lbs Benzisothiazolin-3-one (Proxel ® GXL/ICI Americas)

The components were charged and mixed at 20°-30° C.

The Premier Mill was charged with 2 mm zirconium silicate beads to 80% of the available volume. The mill was preheated to 55° C. by passing hot water through the mill chamber. Simultaneously, the mill shaft was started at 1350 RPM, lime slurry feed was started at 2.17 lb/min., and molten fatty acid feed was started at 2.32 lb/min. rate. The average retention time (ART) in the mill was 3.8 min. The temperature of the exiting material was controlled at 85° C. by cooling water applied to the jacket of the mill. As the material exited the mill, it was passed through a static mixer where 0.33 lb/min. of the additive feed was added. The product was cooled to room temperature by passing through a heat exchanger.

EXAMPLE 14

Lime Slurry Feed

TABLE

| EX-AMPLE | ART (MIN) | PROD. RATE (LB/MIN) | MILL OPERATING CONDITIONS | | | PRODUCT PROPERTIES | | | |
|---|---|---|---|---|---|---|---|---|---|
| | | | % BEAD LOAD | RPM | TEMP (°C.) | % SOLIDS | VISCOSITY | ALK (% KOH) | % SCREEN |
| 1 | 8.9 | 1.72 | 90 | 1650 | 70 | 47.7 | 360 CPS | 1.00 | 0.0000 |
| 2 | 12.4 | 1.77 | 60 | 1100 | 85 | 50.0 | 275 CPS | 0.44 | 0.0013 |
| 3 | 5.2 | 3.53 | 75 | 1650 | 85 | 49.5 | 350 CPS | 0.21 | 0.0002 |
| 4 | 6.1 | 3.63 | 60 | 1100 | 55 | 50.5 | 750 CPS | 0.20 | 0.0120 |
| 5 | 3.6 | 5.90 | 60 | 1100 | 80 | 48.1 | 975 CPS | 1.90 | 0.0060 |
| 6 | 4.0 | 5.19 | 60 | 1650 | 60 | 49.0 | 625 CPS | 0.65 | N/A |
| 7 | 3.8 | 5.46 | 60 | 1650 | 70 | N/A | 150 CPS | 1.20 | 0.0020 |
| 8 | 4.2 | 4.72 | 60 | 1650 | 70 | 55.3 | 395 CPS | 1.51 | 0.0040 |
| 9 | 4.2 | 5.48 | 55 | 1650 | 75 | 55.3 | 270 CPS | 1.02 | 0.0040 |
| 10 | 3.8 | 5.48 | 65 | 1650 | 75 | 55.5 | 355 CPS | 0.36 | 0.0030 |
| 11 | 3.3 | 4.86 | 90% ZIR SIL | 1650 | 85 | 55.5 | 290 CPS | 0.33 | 0.0026 |
| 12 | 3.8 | 4.84 | 80% ZIR OX | 1650 | 95 | 56.5 | 150 CPS | 0.19 | 0.0040 |
| 13 | 3.8 | 4.82 | 80% ZIR SIL | 1350 | 85 | 56.2 | 270 CPS | 0.37 | 0.0030 |
| 14 | 3.8 | 4.85 | 80% GLASS | 1350 | 95 | 55.2 | 305 CPS | 0.18 | 0.0030 |

ALK-ALKALINITY EXPRESSED AS % KOH, MEASURED 1-24 HRS AFTER REACTION
% SCREEN - % OF METAL SOAP RETAINED ON A 325 mesh SCREEN
ART - AVERAGE RETENTION TIME MINUTES
*ZIR SIL = ZIRCONIUM SILICATE BEADS
ZIR OX = ZIRCONIUM OXIDE BEADS
ALL OTHER BEADS ARE GLASS
ALK = ALKALINITY EXPRESSED AS % KOH, MEASURED 1-24 HRS AFTER COMPLETION
% SCREEN = RETENTION ON A 325 MESH SCREEN (DAY BASIS)

542 Lbs Water
92.7 Lbs Hydrated Lime (MV300/Mississippi Lime Co.)
6.5 Lbs Peg 600 Monolaurate (Nopalcol® 6-L/Henkel Corp.)
Agitation was started and the temperature adjusted to 20°–30° C.

Fatty Acid Feed 658.5 Lbs C$_{18}$ fatty acid (Industrene® 7018/Witco Chemical)
45.6 Lbs Ethoxylated Non Phenol (Hyonic® PD-100/Henkel Corp.)
3.5 Lbs C$_{36}$–C$_{54}$ dimer/trimer fatty acid (Empol® 1022/Emery Chemicals)
2.5 Lbs sodium salt of an alkyl aryl sulfonate (Witconate® 1238/Witco)
15.5 Lbs Peg 600 Monolaurate (Nopalcol® 6-L/Henkel Corp.)

The vessel was heated until the charge was molten, agitation was started and the temperature adjusted to 80°–85° C.

Additive Feed 64.8 Lbs Water
54.4 Lbs Peg 600 Monolaurate (Nopalcol® 6-L/Henkel Corp.)
0.8 Lbs Benzisothiazolin-3-one (Proxel® GXL/ICI Americas)

The components were charged and mixed at 20°–30° C.

The premier Mill was charged with 1.5 mm glass beads to 80% of the available volume. The mill was preheated to 55° C. by passing hot water through the mill chamber. Simultaneously, the mill shaft was started at 1350 RPM, lime slurry feed was started at 2.16 lb/min., and molten fatty acid feed was started at 2.36 lb/min. rate. The average retention time (ART) in the mill was 3.8 min. The temperature of the exiting material was controlled at 95° C. by cooling water applied to the jacket of the mill. As the material exited the mill, it was passed through a static mixer where 0.33 lb/min. of the composition in the additives tank was added. The product was then cooled to room temp. by passing through a heat exchanger.

We claim:

1. A continuous process for preparing an aqueous dispersion of a metal soap which comprises: forming a mixture by continuously introducing at least one carboxylic acid having from about 6 to about 30 carbon atoms, at least one oxide or hydroxide of a metal, which forms a metal soap with the at least one carboxylic acid, water and a dispersive amount of at lease one dispersing agent into a media mill, wherein water comprises from about 25% to about 65% by weight of the mixture and reacting the mixture in the media mill for from about 1 to about 55 minutes to form an aqueous dispersion of the metal soap.

2. A process of claim 1 wherein the at least one carboxylic acid is selected from the group consisting of 10 to 22 carbon atom monocarboxylic acids.

3. A process of claim 1 wherein the at least one oxide or hydroxide of a metal is selected from the group consisting of oxides and hydroxides of aluminum, baruim, calcium, cadmium, cobalt, copper, iron, lead, lithium, magnesium, magnese, nickel, strontium and zinc.

4. A process of claim 1 wherein the reaction is carried out at a temperature of from about 25° C. to about 100° C.

5. A process of claim 1 wherein the water, at least a portion of the dispersing agent and the oxide or hydroxide of the metal are introduced into the media mill as a mixture.

6. A process of claim 1 wherein at least a portion of the dispersing agent is introduced into the media mill admixed with the carboxylic acid.

7. A process of claim 1 which comprises: forming a feed mixture comprising the oxide or hydroxide of the metal, water and at least a portion of the dispersing agent; continuously introducing the feed mixture and molten carboxylic acid into the media mill to form the mixture; and reacting the mixture in the media mill at a temperature from about 35° C. to about 95° C. for from about 1 to about 20 minutes to form the aqueous dispersion of the metal soap.

8. A process of claim 7 wherein a portion of the dispersing agent is mixed with the carboxylic acid before the carboxylic acid is introduced into the media mill.

9. A process of claim 8 wherein the dispersing agent comprises from about 0.5 to about 20% by weight of the mixture.

10. A process of claim 1 wherein the acid is stearic acid and the metal hydroxide is calcium hydroxide.

11. A process of claim 1 wherein the temperatures of the material in the media mill is above the melting point of the carboxylic acid.

12. A process of claim 1 wherein the temperature of the material in the media mill is below the melting point of the carboxylic acid.

13. A process of claim 1 wherein the media mill is a horizontal stirred media mill.

14. A process of claim 13 which comprises:

a) forming a mixture of water, dispersing agent and metal oxide or hydroxide;

b) forming a mixture of a fatty acid having from about 8 to about 30 carbon atoms and dispersing agent at a temperature at which the mixture is molten;

c) continuously introducing a) and b) into the media mill, maintained at a temperature of from about 35° C. to about 95° C. and reacting a) and b) for from about 1 to about 20 minutes; and d) recovering as aqueous metal soap dispersion.

15. A process of claim 14 wherein the temperature in the media mill is below the melting point of the fatty acid dispersion agent mixture.

16. A process of claim 14 wherein the temperature in the media mill is above the melting point of the fatty acid dispersion agent mixture.

* * * * *